(12) United States Patent
Rodgers et al.

(10) Patent No.: US 9,037,413 B1
(45) Date of Patent: May 19, 2015

(54) SYSTEM AND METHOD OF VISUALIZATION OF SPECIES CHARACTERIZATION, DYNAMICS AND STRATIFICATION OF THE MAGNETOSPHERE

(75) Inventors: Christopher T. Rodgers, Adamstown, MD (US); Omid E. Kia, North Bethesda, MD (US)

(73) Assignee: EXELIS, INC., Mclean, VA (US)

( * ) Notice: Subject to any disclaimer, the term of this patent is extended or adjusted under 35 U.S.C. 154(b) by 1255 days.

(21) Appl. No.: 12/902,481

(22) Filed: Oct. 12, 2010

(51) Int. Cl.
*G01S 17/89* (2006.01)
*G01S 17/95* (2006.01)
*G01S 13/95* (2006.01)
*G01S 17/88* (2006.01)

(52) U.S. Cl.
CPC ............ *G01S 17/95* (2013.01); *G01S 17/88* (2013.01); *G01S 13/95* (2013.01)

(58) Field of Classification Search
CPC ......... G01S 17/88; G01S 17/95; G01S 13/95; G01W 1/00
USPC ................. 702/2, 3; 250/459.1; 356/3, 4.01
See application file for complete search history.

(56) References Cited

U.S. PATENT DOCUMENTS

| | | | |
|---|---|---|---|
| 5,673,366 A | 9/1997 | Maynard et al. | |
| 5,796,611 A | 8/1998 | Ochiai et al. | |
| 5,943,629 A | 8/1999 | Ballard et al. | |
| 6,023,223 A | 2/2000 | Baxter, Jr. | |
| 6,104,582 A | 8/2000 | Cannon et al. | |
| 6,472,869 B1* | 10/2002 | Upschulte et al. | ............ 324/304 |
| 6,581,008 B2 | 6/2003 | Intrilligator et al. | |
| 6,816,786 B2 | 11/2004 | Intrilligator et al. | |
| 7,096,121 B2 | 8/2006 | Intrilligator et al. | |
| 8,193,968 B1* | 6/2012 | Kia et al. | ............ 342/26 A |

OTHER PUBLICATIONS

Redorbit News, "Alaska Radar System Aids Research on Space Weather, Solar Storms;" http://www.redorbit.com/news.display/?id=1698772, Jun. 2, 2009.
V. Lakshmanan, V. Debrunner, R. Rabin, Texture-Based Segmentation of Satellite Weather Imagery, National Severe Storms Laboratory, U. of Oklahoma, U. of Wisconsin, Madison, *Image Processing*, 2000. Proceedings. 2000 International Conference on, Issue Date: Sep. 10-13, 2000, pp. 732-735 vol. 2.

(Continued)

*Primary Examiner* — Manuel L Barbee
(74) *Attorney, Agent, or Firm* — RatnerPrestia (57) ABSTRACT

A method for collecting data of species in the magnetosphere includes the steps of: (a) tuning at least one laser to spectral indices of targeted atomic or molecular species located in the magnetosphere; and (b) measuring fluorescence radiation from each of the targeted species, in response to the tuning step. The method determines range to each of the targeted species. The method geo-locates the species with respect to the Earth to provide a registered map of the targeted species in three dimensions (3D) with respect to the Earth; and temporally trends each of the targeted species to provide the registered map in four dimensions (4D). The method may also determine abundance from multiple wavelengths returned from the fluorescence radiation of the targeted species.

20 Claims, 9 Drawing Sheets

(56) References Cited

OTHER PUBLICATIONS

E. Bratsolis, M. Sigelle, "Solar Image Segmentation by Use of Mean Field Fast Annealing," Astronomy & Astrophysics Supplement Series, 131, 371-375, Aug. 1998.

Rick Archibald, Jiuxiang Hu, Anne Gelb and Gerald Farin; "Improving the Accuracy of Volumetric Segmentation Using Pre-Processing Boundary Detection and Image Reconstruction", IEEE Transactions of Image Processing, vol. XX, No. Y, Month 2003.

* cited by examiner

SYSTEM AND METHOD OF VISUALIZATION OF SPECIES CHARACTERIZATION, DYNAMICS AND STRATIFICATION OF THE MAGNETOSPHERE

TECHNICAL FIELD

The present invention relates, in general, to systems and methods for characterizing the Earth's magnetosphere. More specifically, the present invention relates to gathering sufficient data, by way of a laser induced fluorescence detection and ranging (LIFDAR) technique and other techniques, to allow for the visualization of species in the magnetosphere, their dynamics, stratification and their geo-location around the globe.

BACKGROUND OF THE INVENTION

The Earth's magnetosphere occupies a region of space in which the Earth's magnetic field dominates the pressure exerted by the solar wind flowing outwardly from the sun. The solar wind includes constantly radiating enormous amounts of energy across the entire electromagnetic spectrum. In addition, the solar wind includes a steady stream of charged particles, such as protons, electrons and neutrons. The magnetosphere is the Earth's geomagnetic field.

The magnetosphere is partially flattened on the sunlit side of the Earth, flattened directly from the pressure applied to the magnetosphere by the solar wind. On the side of the Earth opposite that facing the sun, however, the geomagnetic field is stretched out, past the Earth, for millions of miles. On the sunlit side of the Earth, the geomagnetic field extends past the Earth for less than ten Earth radii.

Adding to the normal energy output from the sun, there are periodic and random solar activities that result in massive increases in ambient energy. The prime events in solar activities are the coronal mass ejection (CME) and the solar flare. A large CME may contain 10 billion tons of matter that is accelerated to several million miles per hour. A solar flare is an explosive release of energy including electromagnetic and charged particles. The energy released is substantial and may be equal to the simultaneous detonation of a trillion five-megaton nuclear weapons.

The Earth's magnetic field deflects some of the solar particles, but at some locations on the Earth, such as above the polar caps, the solar particles interact with the near-Earth environment. However, when strong solar winds sweep past the Earth, they cause shockwaves to ripple through the magnetosphere.

Geomagnetic storms cause rapid fluctuations in the Earth's magnetic field and increase the amount of ionized particles impinging on the Earth's ionosphere. These rapid fluctuations may cause failure of power grids on the Earth, orientation errors in navigation systems relying on magnetic compasses, and sporadic or total blackouts of communication systems. In addition, satellites relying on optical sensors to gaze at stars to maintain orientation in space may be vulnerable to cosmic rays and high-energy protons. These energy protons may produce flashes of light, causing false-star detection and attitude errors with respect to the Earth.

Furthermore, a geomagnetic storm or proton event may physically damage a launch vehicle or its payload. The electrostatic charge deposited on the vehicle may be discharged by onboard electrical activity, such as vehicle commands from a flight control system. In fact, with newer microelectronics and their lower operating voltages, it is actually easier to cause electrical upsets than on older, simpler vehicles.

Due to limitations in available data, such as stratification of ionized species and their dynamics, very little has been done to effectively visualize or even represent dynamics of space weather. Current understanding is primarily limited to insitu measurements of species, tabular specifications of energy doses and capture of solar events. The current visualization of space weather and its dynamics revolve around mathematical modeling and simulation of various parts of the space weather system. The result is a very coarse, limiting and, at times, inaccurate representation of what actually happens. For example, in a Google Earth's depiction of space weather, the Earth's atmosphere is represented as an even spherical cover having color coding depicting energy levels or electron density. The specific ionic species, densities and interactions are not shown, and the resolution of distinguishing patterns are extremely large and cover entire continents at a time.

What is needed is a method and system for gathering sufficient data that is accurate enough to describe and visualize space weather including the volume of species, their dynamics and their geospacial coverage around the globe. The present invention addresses this need.

SUMMARY OF THE INVENTION

To meet this and other needs, and in view of its purposes, the present invention provides a method for collecting data of species in the magnetosphere. The method includes the steps of:

(a) tuning at least one laser to spectral indices of targeted atomic or molecular species located in the magnetosphere;

(b) measuring fluorescence radiation from each of the targeted species, in response to the tuning step; and (c) determining range to each of the targeted species.

Step (b) includes measuring scattered radiation from each of the targeted species, in response to the tuning step. Step (c) includes normalizing the fluorescence radiation based on the scattered radiation; and determining the range from the normalized fluorescence radiation to each targeted species.

Step (a) may include tuning at least two lasers to multiple wavelengths. Step (b) may include determining abundance from the multiple wavelengths returned from the fluorescence radiation of the targeted species.

The method may also include collecting data from the fluorescence radiation for determining temperature of the targeted species; and collecting data from the fluorescence radiation for determining drift velocity of the targeted species.

The method may scan the laser in azimuth and elevation to obtain a 2-dimensional location of the targeted species; and obtain a 3-dimensional location of the targeted species, after determining the range.

The steps of tuning, measuring and determining of steps (a), (b) and (c), respectively, may be performed in a space location, on an Earth location, or in both locations. In addition, at least one laser may be located in space and another laser may be located on the Earth.

Another embodiment of the present invention is a method for obtaining data related to species in the magnetosphere. The steps include:

a) tuning at least one laser to spectral indices of targeted atomic or molecular species located in the magnetosphere;

b) measuring instantaneous scattering and fluorescence radiation from the targeted species, in response to the tuning step;

c) determining dynamic range to each of the targeted species producing the scattered radiation;

d) determining dynamic normalization of the fluorescence radiation from the scattered radiation; and e) determining dynamic range based on the normalized fluorescence radiation to each of the targeted species.

The step of tuning the laser may include scanning the laser to different wavelengths based on the targeted species.

The method may further include one, or more than one, of the following steps:

identifying the targeted species, based on returned wavelengths of the radiation;

determining changes in stratification of the targeted species as a function of time;

determining changes in abundance of the targeted species as a function of time;

determining changes in temperature of the targeted species as a function of time; and determining changes in drift velocity of the targeted species as a function of time.

Yet another embodiment of the present invention is a method for obtaining data of species in the magnetosphere. The method includes the steps of:

collecting, during a first period, a first dataset of tuples for each of multiple species located in the ionosphere, each tuple defined by a first respective point in a coordinate system referenced to the Earth;

collecting, during a second period, a second dataset of tuples for each of the multiple species located in the ionosphere, each tuple defined by a second respective point in the coordinate system referenced to the Earth;

determining dynamic variations as a function of position and velocity between the first and second datasets of tuples in the coordinate system referenced to the Earth; and predicting a third dataset of tuples for each of the multiple species, during a third period, based on the first and second datasets.

The following steps may also be included:

determining a first density of each of the multiple species, based on the collected first dataset of tuples;

determining a second density of each of the multiple species, based on the collected second dataset of tuples;

determining temporal density variation of each of the multiple species, based on the determined first and second density;

extrapolating intensities of electromagnetic fields in a local vicinity of the first and second datasets of tuples, based on a global model of electromagnetic field intensities in the magnetosphere;

determining temporal variations of intensities of electromagnetic fields between the first and second periods, and estimating temporal variation of intensities of electromagnetic fields during the third period.

The method further geo-locates the species with respect to the Earth to provide a registered map of the species in three dimensions (3D); and trends each of the species to provide the registered map in four dimensions (4D).

Still another embodiment of the present invention is an interactive information visualization system including:

a first database including at least one model relating to the magnetosphere, a second database including data of multiple species located in the magnetosphere, a processor for combining the model from the first database with the data from the second database, and a visualization module, coupled to the processor, for providing space weather to an end user.

Data in the second database includes location of a species with respect to a geographical reference to the Earth. The data includes three dimensional coordinates of the species, and density of the species. The model represents an interaction between the species and electromagnetic fields in the magnetosphere. The electromagnetic fields are modeled based on solar observations from the Earth.

The processor interpolates strength of the electromagnetic fields at the three dimensional coordinates of the species. The visualization module provides temporal dynamics of the electromagnetic fields, on a level localized to the three dimensional coordinates.

The second database includes a dataset defined by multiple tuples (x, y, z), each occupying a space for each (x, y, z) data point sampled of a species located in the ionosphere. The visualization module includes a boundary between each species based on the multiple tuples. The dataset includes an identification of the species at each of the tuples, and density data of the multiple tuples belonging to each respective species. The dataset may include movement speed and direction at multiple tuples.

It is understood that the foregoing general description and the following detailed description are exemplary, but are not restrictive, of the invention.

BRIEF DESCRIPTION OF THE FIGURES

The invention may be understood from the following detailed description when read in connection with the accompanying figures.

DETAILED DESCRIPTION OF THE INVENTION

Figure 1:
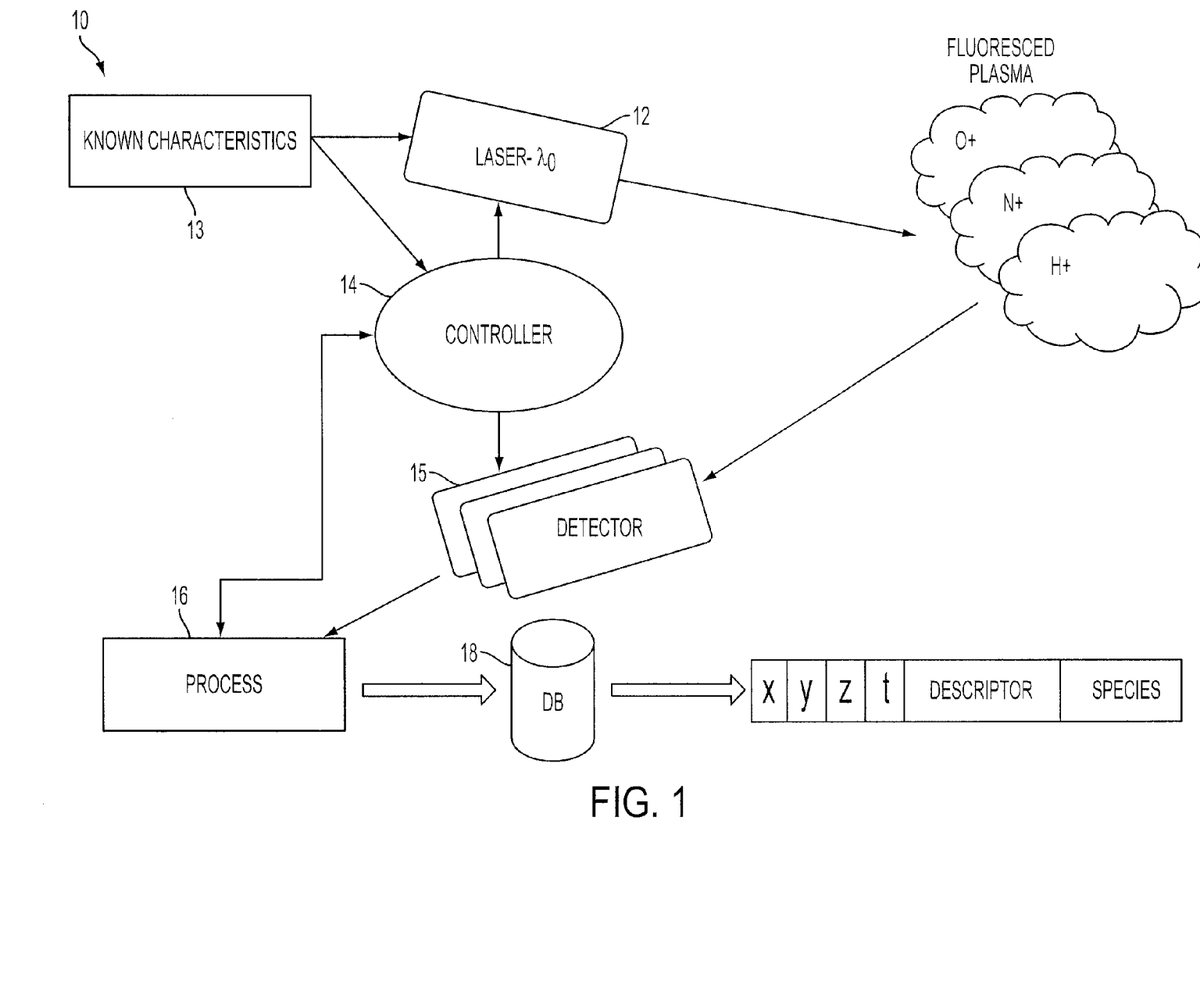
FIG. 1 is a laser induced fluorescence detection and ranging (LIFDAR) system for collecting data, including three dimensional orientations of vario us species in the magnetosphere including their temporal variations, in accordance with an embodiment of the present invention.

Referring first to FIG. 1, there is shown a laser induced fluorescence detection and ranging (LIFDAR) data collection system. As shown, system 10 includes tuned laser 12, controller 14, detector 15, processor 16 and database 18. The system 10 is described in detail below.

The tuned laser 12 is a coherent light source that is constructed by energy transition of electrons in atoms and molecules from a high energy state to a lower energy state (or difference of energy states), E1–E2. This transition produces a quantum of energy in the form of a photon at a specific wavelength given by:

$$E1 - E2 = \frac{hc}{\lambda_0} \quad (1)$$

where $\lambda_0$ is the output wavelength of the tuned laser,
h is Plank's constant, and c is the speed of light.

Through constant stimulation of these atoms or molecules, the photons are produced at a constant rate to generate light at the most probable energy transitions. The laser 12 is tuned to desired wavelengths by stimulating the electron energy transitions to correspond with a desired wavelength, combined with prism multiplying techniques. The laser may be tuned to desired wavelengths by using a database of known characteristics, generally designated by 13, which provides the required transmitting wavelengths from the laser toward the gas or plasma, such as oxygen, nitrogen and hydrogen ions, to produce fluorescence at respective excitation energy levels.

It will be appreciated that laser induced fluorescence is an active spectroscopic method used for studying structures of molecules, detection of atomic and molecular species, and velocity measurements within a gas or plasma. The laser 12 may be tuned by controller 14 to a desired wavelength of the species' electron excitation energy level. After some time (a few nanoseconds to microseconds), the electrons of the excited atomic or molecular species de-excite and emit light at a wavelength larger than the excitation wavelength. The wavelength is dependent upon the energy level transition of the electrons and the probability that the electron will de-excite to that energy state. This light, or fluorescence, may then be measured by detector 15, or several detectors 15 for the multiple wavelengths transmitted by laser 12.

The detection and ranging of light emissions is based on time of flight measurements. This is commonly found in LIDAR systems where the processed data may be intensity as a function of range. The range may be calculated based on the time of flight of the photon from laser source 12 to the excited species and back to detector 15.

In the example shown in FIG. 1, for light induced fluorescence data, the laser 12 transmits pulses at a specific pulse rate and a specific phase. The corresponding fluorescence also has its own rate of intensity variations and likely a different phase. By measuring the intensity variation of the fluoresced gas or plasma, a curve depicting light intensity verses time may be generated. The light curve has its own associated phase, which is different from the phase of the original transmitted laser pulse. This phase difference provides a time difference, which corresponds to the time of flight. This time of flight provides the range to the fluoresced gas or plasma.

In the embodiment shown in FIG. 1, processor 16 receives the detected data from each fluoresced plasma and computes the range to each species. A look up table (LUT) may also be generated and stored in database 18, which includes range to each identified species, which may be identified based on the transmitted laser wavelength and the fluoresced wavelength from the species. The processor may also generate and store an LUT that includes geo-referenced range to the identified species. Accordingly, three dimensional (3D) data in an x, y, z coordinate system may be generated for each species, where x and y are horizontal coordinates with respect to the Earth and z is altitude with respect to the Earth. Similar received data processed over a period of time allows for four dimensional (4D) data in an x, y, z, and t coordinate system per species, as shown in FIG. 1.

Figure 2:
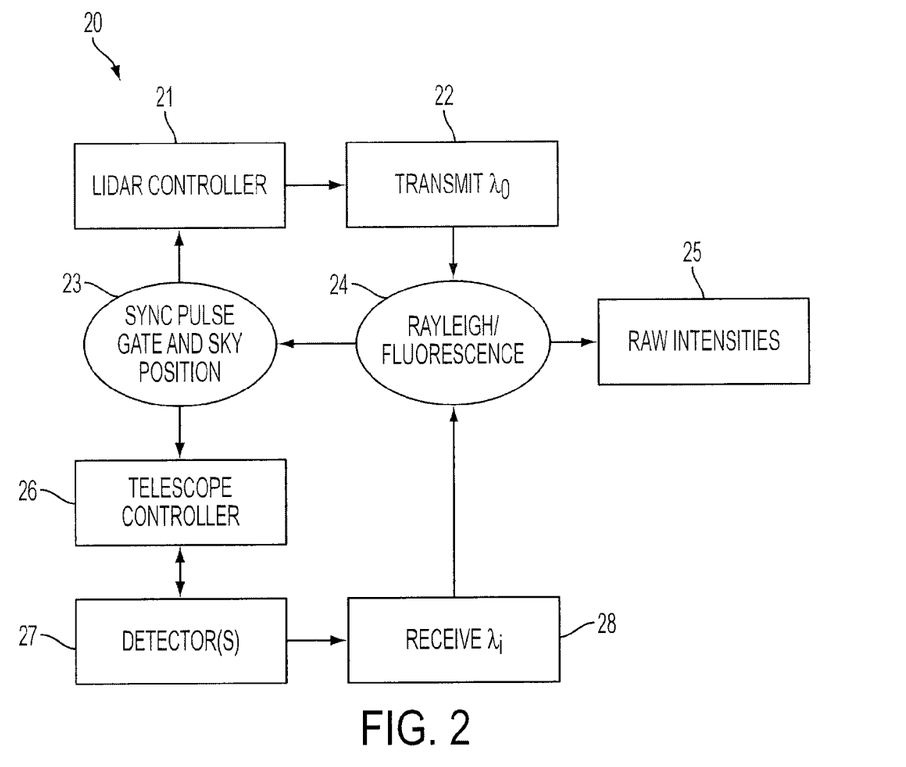
FIG. 2 is a block diagram depicting a process for collecting raw intensity data of various species in the magnetosphere, in accordance with an embodiment of the present invention.

Referring next to FIG. 2, there is shown another system, designated as 20, for producing raw intensities, or raw data from species in the magnetosphere. A LIDAR system including controller 21 generates a pulsed signal directed to a species. The pulsed signal is synchronized, by way of synchronizer module 23, to the sky position of a telescope including telescope controller 26. The LIDAR transmits the pulsed signal at a first wavelength of $\lambda_0$ toward the species by transmitter 22. The LIDAR system then receives a fluoresced signal from the species at a wavelength of $\lambda_i$ by receiver 28. The received signal is detected by a one or more detectors 27. The detected data includes raw fluorescence intensities and raw Rayleigh intensities, finally outputted by module 24.

The fluoresced energies are directly related to the number of electrons transitioning from the excited state to the lower recorded state at the wavelength $\lambda$. Using two different wavelengths that are longer than the original transmitted wavelength, $\lambda_0$, the Boltzmann Equation may be solved to obtain the number of atoms or molecules that are singly ionized, assuming local thermodynamic equilibrium.

Figure 3:
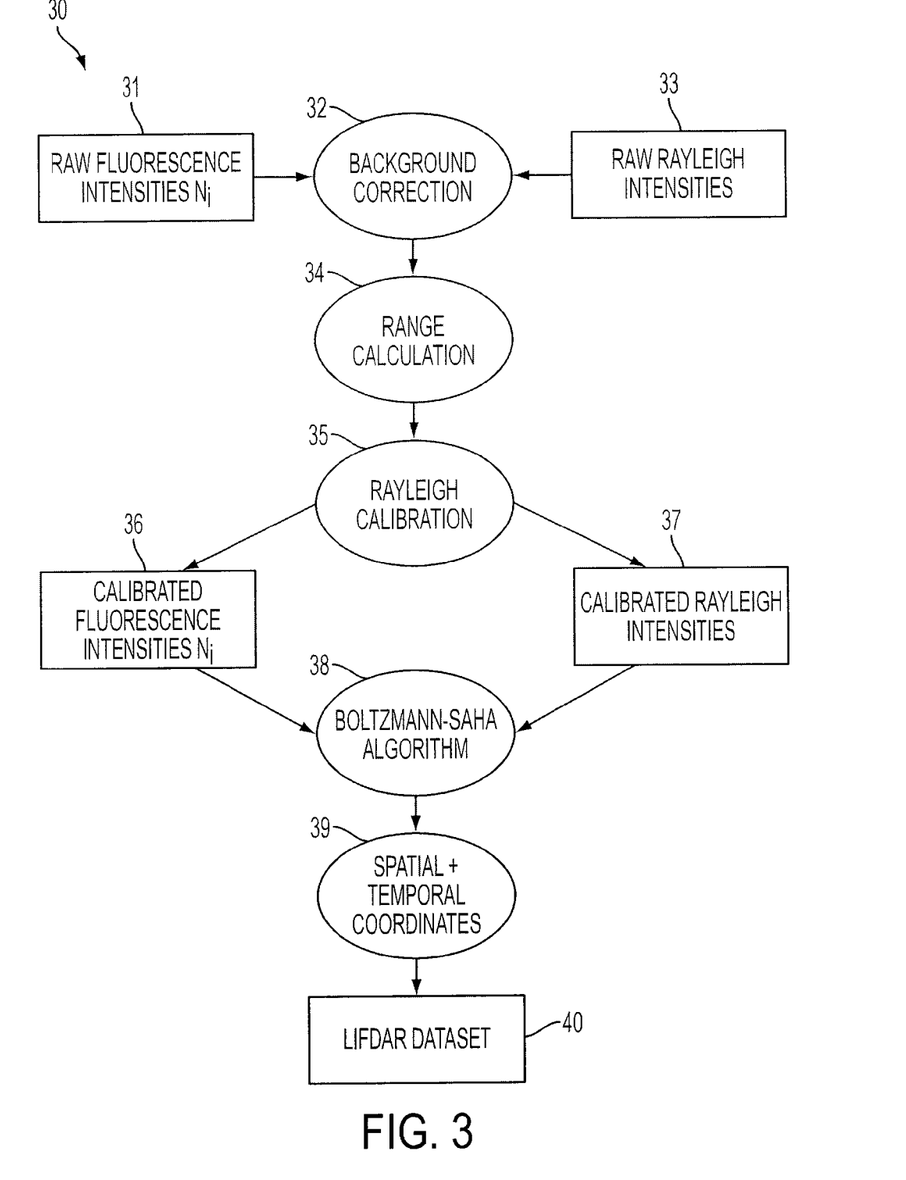
FIG. 3 is a block diagram of a method for collecting, processing and calibrating data to form a dataset for use in visualizing the magnetosphere and for space weather predictions.

An example of calibrating luminosity of the fluorescence to determine chemical abundance for atomic and molecular species is provided in FIG. 3. As shown, the raw fluorescence intensities, received by module 31, and the raw Rayleigh intensities, received by module 33, are corrected for background noise by module 32. Based on range calculation, by module 34, and Rayleigh calibration, by module 35, calibrated values for the fluorescence intensities (module 36) and Rayleigh intensities (module 37) are obtained.

Using the LIDAR equation for resonance fluorescence and the range calculations, the number of ions in a specific energy state may be calculated. The LIDAR equation for fluorescence is as follows:

$$N_I(z) \sim N_R(z_R) \frac{F_S(\lambda i, z) - F_B \delta t}{FR(\lambda i, z_R) - F_B \delta T} \frac{z^2}{z_R^2} X_{eff} \quad (2)$$

where
$N_I$ is the density of an ion species as a function of range, z,
$N_R$ is density of atoms or molecules from Rayleigh scattering,
$F_S$ is the fluorescence signal,
$F_R$ is the Rayleigh scattering signal,
$F_B$ is the background noise,
z is the range of the fluoresced ions,
$z_R$ is the range to the Rayleigh scattered atoms or molecules,
$\lambda_i$ is the fluorescence wavelength, and
$X_{eff}$ is the effective extinction of the atmosphere at $\lambda_0$.

The Rayleigh scattering is included in Equation 2 to effectively calibrate the intensity of the fluorescence signal, so that the absolute illuminating energy may be calculated to give $N_i$.

By using Equation 2 for both the ion and neutral atom or molecule species, the free electron density (Ne) may also be calculated via the Boltzmann-Saha algorithm, as shown by module 38.

Given that the absolute electron density is produced by all ion species in the atmosphere at altitude z, the free electron density measured by fluorescing the most abundant molecular species is a statistical lower limit at that altitude. This is useful in that lower limits to the electron density at any given altitude is measured. In contrast, radio frequency (RF) techniques, in use today, are unable to distinguish between species and only obtain the largest signal return, representing one altitude.

By tuning the laser to known spectral indices of the atomic or molecular species (which may be taken from database 13), the gas is fluoresced and the emission of the fluorescence may be captured by a detector. Based on several returns, a phase difference between the laser pulse and the light curve of the fluorescence may be established. This phase difference provides the time of flight, from which the range to the fluoresced gas or plasma may be determined. Gathering this type of data as a function of time provides the end user with species abundance, range, and its dynamics (position and velocity as a function of time) at various spatial coordinates (module 39). The final LIFDAR dataset may be stored in module 40 and may include geo-referenced x, y, z data for each species as a function of time and density of each species.

Based on scanning rate, capacity and geo-location, there may be locations on the Earth that require approximations. The present invention contemplates extrapolating the dynamics and temporal relationships of the sampled data to areas that are not fully covered. For example, Earth bound scanners may have large areas that are not covered over large water masses. However, by knowing how species interact and the temporal aspects of the system, the present invention may extrapolate the conditions over these areas with higher accuracy than what is currently available.

In addition, an aspect of space weather that is prevalent today is the mathematical modeling of the interaction between matter and electromagnetic fields. All of these models, however, rely on solar observations and do not have access to immediate and local data. The level of processing contemplated by the present invention is an increase in the available data, based on newly acquired local data. This makes a profound effect on the space weather modeling efforts. In essence, a form of finite element analysis becomes possible. This is because a higher level of system perturbation parameters are made available on a smaller scale which, in turn, allow small elements to be modeled with a small set of dynamics. This is in contrast with a large system dynamics which controls the science today. The range of processing that is contemplated by the present invention greatly increases the available data of today.

Species discrimination may also open up a range of processing geared towards weather forecasting. With a higher level of detail into the dynamics of the magnetosphere, coupled with the existing knowledge of dynamics and temporal information, the present invention provides a higher level of space weather forecasting capability.

Due to limitations in available data, such as stratification of ionized species and their dynamics, very little has been done to effectively visualize or even represent dynamics of a system for space weather. Current understanding is primarily limited to in situ measurements of species, tabular specification of energy dose and capturing of solar events. The current visualization of the system and its dynamics revolve around mathematical modeling and simulation of various parts of the system based on these limited data sources. The result is a very coarse, limiting and, at times, inaccurate representation of what actually happens.

Figure 4A:
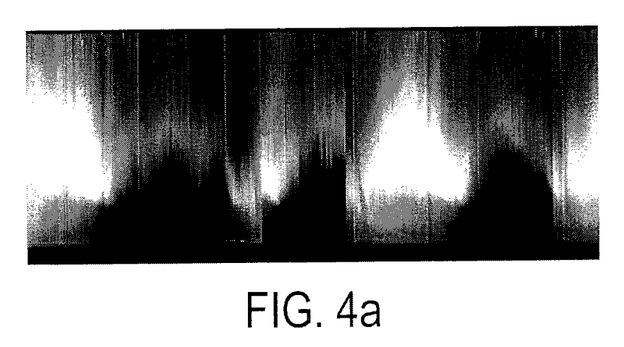
FIG. 4a is a layer stratification of intensity levels of ionic species in the ionosphere.
Figure 4B:
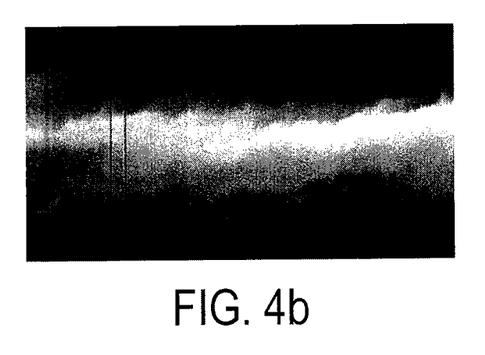
FIG. 4b is a depiction of potassium concentration in the upper atmosphere.

The present invention contemplates stratification of the ionized species and their dynamics as a function of time. For example, FIG. 4a depicts a vertical pattern that shows the Northern lights in stratified layers. The figure shows varying amount of densities as a function of altitude, when visualizing the ionic species content of the ionosphere. FIG. 4b shows stratification of potassium concentration in the upper atmosphere of the Earth in vertical slices. Thus, the stratification of species in the ionosphere (for example) by the present invention provides a much more elaborate and detailed depiction of space weather than is presently provided by the simplistic depiction of space weather presented by Google Earth.

Similarly, when visualizing species content, a three dimensional gas plume similar to that available from various fluid mechanisms may be obtained by the present invention. Such a three dimensional depiction of species content is missing from current capabilities. Detailed visualization of species in the ionosphere, however, is now possible by obtaining a resolved data set, in both time and space, with different devices, such as a LIFDAR scanner. A highly resolved data set, in time and space, allows a realistic visualization of the ionosphere not possible before.

Parallelism may be made between visualization of tornados before and after discovery of tornado dynamics. Before such discovery, a tornado's internal workings were not known and the complex air and water convection were also not known and, thus, could not be visualized. Driven by the need to realistically predict the formation and life of a tornado, various visualizations were considered and used to come up with a set of solutions. Some of these solutions are currently relied on to predict weather in the atmosphere. The same is true for space weather predictions.

Figure 5:
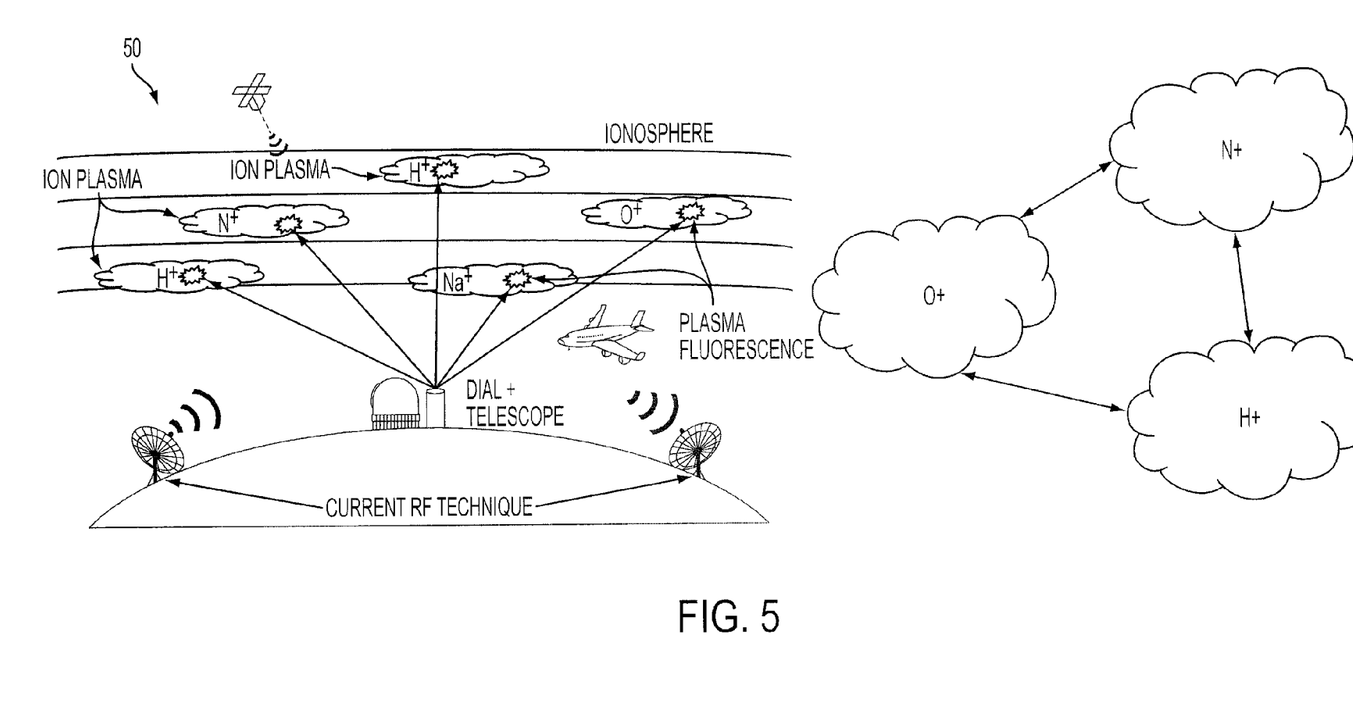
FIG. 5 is a functional diagram of multiple systems used for collecting data of various species located in different layers of the ionosphere, in accordance with an embodiment of the present invention.

The current state of visualization is limited to the available set of data, which is mostly dependent on mathematical models. By providing a stratified (layered) data source, however, a three dimensional aspect of space weather may be realized. Furthermore, species discrimination in a stratified manner allows a higher level of diagnostic access to data that has not been done before. Even for Earth weather, the amount of species discrimination is limited to vapor content. The present invention, however, allows discrimination between many species, such as nitrogen, oxygen and hydrogen, thereby providing capabilities of visualization orders of magnitude better than what is currently available. Other aspects of sensing, such as temperature, velocity, ionization, and temporal relationships may also be captured and then visualized. A system, designated as 50, for capturing data from the ionosphere, as an example, to provide visualization of space weather is shown in FIG. 5. As shown, system 50 includes at least one LIDAR system coupled with a telescope (shown in more detail in FIGS. 1 and 2), which are used to stratify various species in the ionosphere as a function of x, y, z coordinates and as a function of their respective temporal changes (time as a variable).

In addition, system 10 also includes at least two RF transmitters, located a large distance from each other, to determine the geo-locations of other species and particles not detectable using laser wavelengths. Details of using RF transmitters for space situational awareness and space weather is disclosed in a related patent application Ser. No. 12/688,299, filed on Jan. 15, 2010, by some of the inventors of the present invention. That Patent Application is incorporated herein by reference in its entirety and is applicable, by extension, to land based antenna and transmitter systems.

Figure 6:
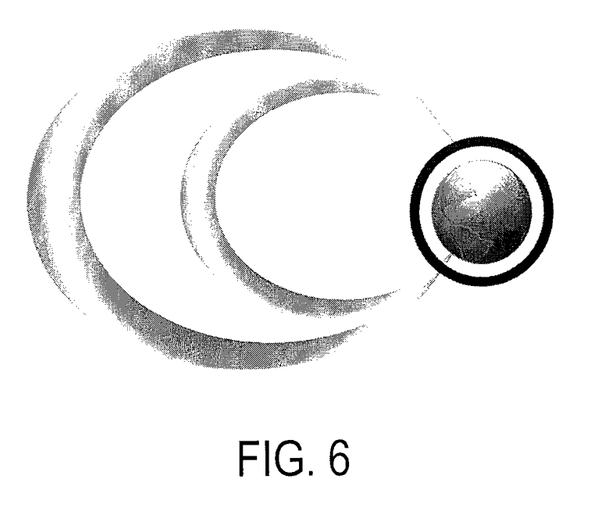
FIG. 6 is a visualization of the Van Allen belts and the ionosphere surrounding the Earth.

In addition to mapping species in the ionosphere as a function of time, the present invention contemplates mapping the entire magnetosphere. For example, there is a relationship between the outer Van Allen belt, inner Van Allen belt and the ionosphere which has been studied and modeled. Missing, however, is an infusion of remotely sensed data with a higher level of detail to describe this relationship. For example, diffusion between the Van Allen belts are described as a uniform diffusion. Current understanding of how much and when this diffusion occurs is missing. The geographical distributions and visualizations that relate the diffusion to other aspects of space weather, such as the remote sensed data of the present invention and existing remote sensed data from solar observers. A general relationship between the Van Allen belts and the ionosphere is shown in FIG. 6.

Figure 7:
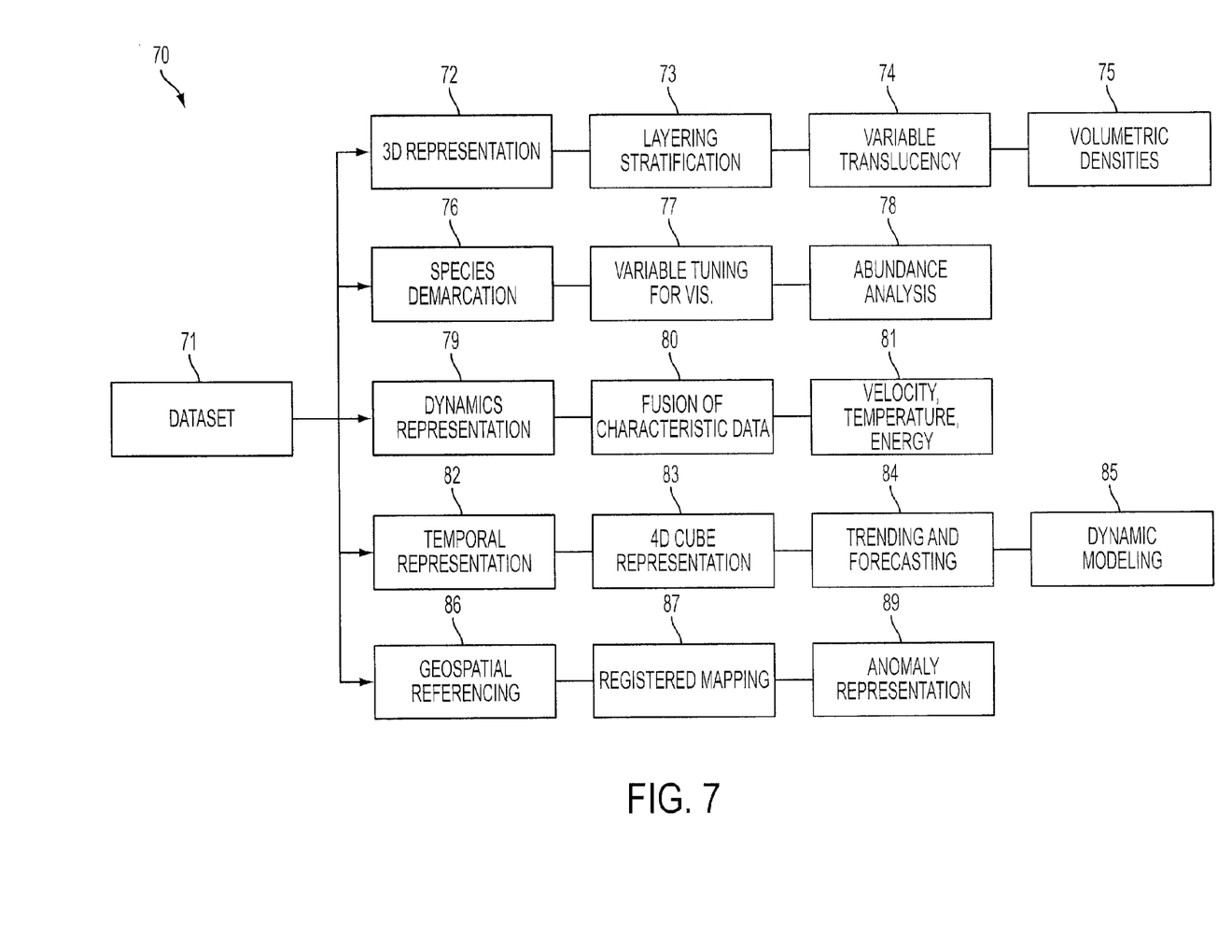
FIG. 7 is a block diagram showing a visualization process for space weather, in accordance with an embodiment of the present invention.

A visualization method of the present invention, generally designated as 70, is depicted in FIG. 7. The method is formed from data contained in dataset 71 which may be obtained, for example, from the systems shown in FIGS. 1, 2 and 3. The method 70 provides species discrimination (aka material composition) in a stratified manner (stratified, for example, in altitude), with geospatial coverage (corresponding to the ground) and dynamic characteristics (aka diffusion layers and hot spots) in a temporal sequence (as a function of time). This is motivated with parallelism to tornado visualization and will benefit airplane route planning, satellite trajectory planning, GPS signal loss estimation, satellite communication loss estimation, satellite longevity determination, etc.

The visualization method shown in FIG. 7 is described below, although it will be understood that other aspects of visualization data may be contemplated and a higher level of visualization may be derived than that shown in FIG. 7. The set of derived steps are similar to concepts used today in earth weather to delineate cold/warm fronts, low/high pressure centers, eye of a hurricane, and the like. At present, dataset 71 is not available, but the present invention contemplates generating the dataset using the systems shown in FIGS. 1, 2 and 3 and then analyzing the available data, including data from dataset 71 and other known available data from conventional methods of weather modeling.

Step 72—Forming 3D Representations of Species

A diagnostic volumetric dataset is preferred over a volumetric surface dataset because it provides information that otherwise may be hidden. In a diagnostic volumetric dataset, the volume is described by a tuple (x, y, z) which occupies the space for each (x, y, z) sample point; a volumetric surface dataset, however, only describes a portion of the tuple (x, y, z) that corresponds to a particular surface, which in space weather represents a detectable discontinuity. Systems, such as Geiger mode LIDAR systems generate only volumetric surface datasets, whereas linear mode LIDAR systems generate diagnostic volumetric datasets. While both datasets may be used for space weather, the present invention prefers a diagnostic volumetric dataset approach.

Visualizing diagnostic volumetric datasets requires segmenting regions having similar characteristics. This may be done by either using density maps or detection regimes to mark boundaries of changes in characteristics. One method of doing this is known as region growing. This method first seeds a starting point in a volume, then grows that point by considering neighboring points exhibiting similar characteristics. The method continues for each newly added point and ends at a point where there exists no more similar points, thereby forming a boundary. Region growing thus creates a metric that marks characteristic boundaries. The resultant species in the ionosphere, for example, now includes a finite boundary that may be used to form a surface and build up to a bounded volume with multiple finite surfaces.

The present invention also cuts through this volume, in order to visualize a layer stratification in a format of the registered data from the dataset (step 73). For example, if the original data includes densities, a virtual cut may visualize changes in densities across each cut. As another example, if the original data includes drift velocity, then an absolute velocity may be visualized in the species grown by the density data. A virtual cut is a basic visualization inside a volumetric space. More complex slicing may be introduced into a volumetric space, such as slicing formed by a fly-through. A fly-through provides a visualization of a volumetric space, as a user flies through the space.

Another element in visualizing a diagnostic volumetric space is in visualization of multiple segmented objects. This is important in situations when one object (species, for example) is completely engulfed by another object and thus may be completely hidden by that object. In order to prevent one object from hiding another object, the present invention includes forming a variable translucency in visualization (step 74). This may be done by assigning a higher level of translucency to the object that surrounds an inner object, so that the inner object becomes visible. The inner object, however, is assigned a smaller level of translucency. One thus may distinguish between different objects.

The method may also include visualizing an object (or species) by using a color scheme with varying levels of translucency. Such visualization, however, does not provide a real texture feel to the surface of the object. Since the dataset may include different data pertaining to volume, the present invention also provides information to synthesize a virtual texture of an object (step 75). This is important when multiple datasets are fused together, such as densities and drift velocities, or density patterns in a density mapped volume. The synthesized texture may be implemented with variations in the surface or with a different color assignment to a specific density.

Step 76—Forming Species Demarcations

Given a dataset that uniquely classifies different parameters and characteristics of species, the present invention separates one species from another by demarcation. As such, a workflow is set to vary these parameters and characteristics in a way that visualizes a physical phenomenon. For example, in the process of a body of a material diffusing into a different type of material, a diffusion layer exhibits lower densities as the individual species transform. Therefore, when two different materials of lower densities are in the same region of space, they most likely are undergoing a chemical process. By varying the threshold in densities that mark the extent of some species, the present invention equalizes the resultant volumes so that the two species may be visualized in relation to each other. If other data, such as drift velocity, is included the species may also be selectively tuned in its local environment (step 77). This provides better visualization with added benefits of dynamic modeling.

Since multiple scanning regimes provide insight into species that have many levels of excited states, abundance analysis (step 78) is performed by the present invention to arrive at a desired solution. This analysis takes into consideration multiple detections that contribute to a single outcome. Such fusion of data is unique to visualization since varying degrees of detections may yield an abundance analysis; many fusion algorithms utilize a strict mixing and registration methodology to derive at a unified result. This is useful in several aspects of planning and analysis, much like determination of the total electron count (TEC), which is used today in ionospheric studies.

Step 79—Forming Dynamic Representations

In forming an understanding of the dynamics of the magnetosphere, the present invention analyzes multiple characteristics of detected points in space. Given at least access to velocity, temperature and energy in the dataset, the present invention fuses relevant parameters to gain a better understanding of the magnetosphere. This is similar to a process in a human organ that consumes and produces species that have unique signatures. For example, overlaying Doppler information on an ultrasound scanned image shows whether the species are moving and the direction of movement. Nuclear imaging, for example, has provided the same type of added functionality by supplementing organ functionality to high definition soft tissue, or hard tissue scanning. An analysis of how the species are created or depleted plays an important role in the dynamics of space weather predictions. The dynamics are visualized by fusing various characteristic data (step 80) and characterizing the velocity, temperature and energy level of each species (step 81).

Step 82—Forming Temporal Representations

A 4D cube representation is used in Earth weather predictions. It indicates the temporal aspects of volumetric data derived from the atmosphere. Space weather data obtained by the present invention mainly parallels Earth weather and forms a 4D cube representation of space weather (step 83). Much like the dynamics and internal visualizations of tornados on Earth, space weather visualization is derived from the dynamic modeling generated by the present invention. Analysis of trends based on ambient conditions produce space weather forecasting (step 84).

Hurricane forecasting includes an analysis of water temperature, atmospheric pressure, jet streams and other factors. Similarly, the present invention analyzes coronal mass ejections, saturation of the Van Allen belts and other factors to provide space weather forecasting. Furthermore, after a coronal mass ejection, where residues of the ejection interact with the Earth's magnetosphere, the present invention predicts the interaction with the ionosphere based on the time delays in the ejection.

Step 86—Forming Geospatial Referencing

Current visualization of space weather is heavily geared towards modeling and simulation. The data detected and processed by the systems depicted in FIGS. 1, 2 and 3 allow higher definition and detail and, thus, may be accurately registered to corresponding points on Earth. Registration to anomalies, poles, equators and other landmarks are used to effectively deliver a suitable product to the end user (step 87).

Since complete coverage is not available at all times, some processes and trends need to be employed to effectively model such regions in space. Given the rich dataset provided by the present invention, it is possible to obtain a high definition of the current space weather, coupled with a higher definition of ground registered points.

The anomalies associated with discontinuities in the magnetic fields and earth rotation is a continuous subject of interest. Currently, there exists little pathway in depicting the relationship between the detected space weather and these anomalies. The present invention, with its rich and accurate dataset, contemplates providing representations of these anomalies (step 89).

Figure 8:
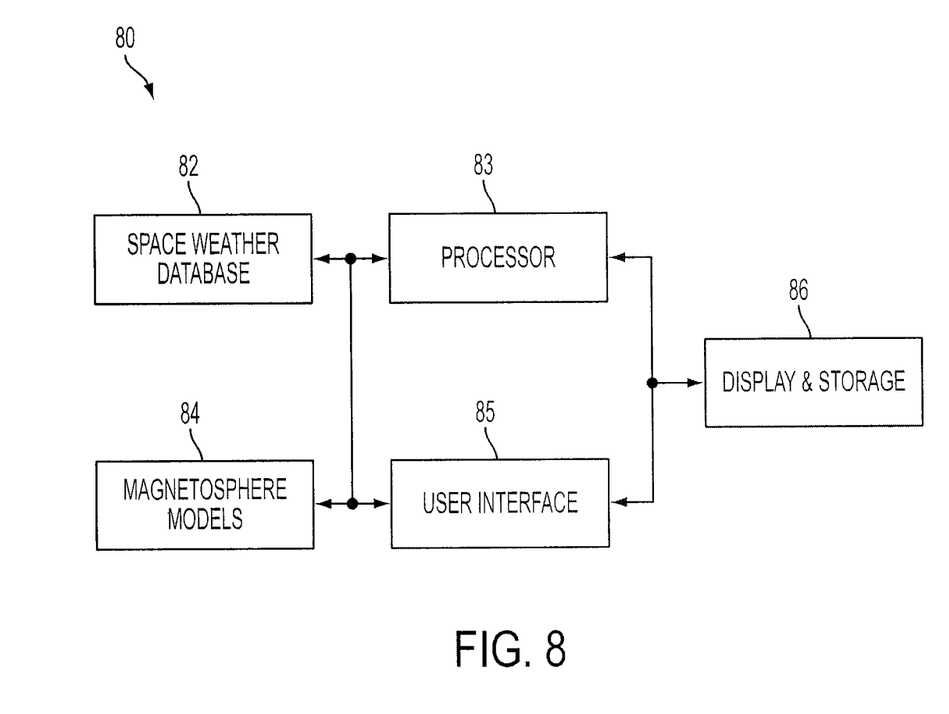
FIG. 8 is a block diagram of an interactive information visualization system, in accordance with an embodiment of the present invention.

Referring next to FIG. 8, an interactive information visualization system, generally designated as 80, includes two databases 82 and 84. The two databases are combined by processor 83 and interactively controlled by user interface 85. The output from processor 83 is provided to display or storage device 86 as desired by the user.

The database 82 includes data of multiple species located in the magnetosphere, and in particular the ionosphere. The data may include the geographic location of each identified species with respect to the Earth, and the density of each identified species. Thus, this database may include sets of tuples in (x, y, z) coordinates for each species collected during different periods of time. Computed differences in the tuples between one period of time and another period of time, executed by processor 83, provides temporal variations in each species and its relationships to one another. These temporal variations may also be stored in database 82. Other parameters, such as the visualization parameters shown in FIG. 7, may also be obtained by processor 83 or by an external processor (not shown). These data may also be stored in database 82. The tuple data for each identified species may be obtained by the LIFDAR system shown in FIG. 1, or by other systems, such as a SAR or a radar system (see FIG. 5), residing on the Earth or borne into space by a satellite.

Thus, accurate tuple data of each species is obtained and stored in database 82. These include real data of locations and densities of the species in localized regions, for example, a region in the ionosphere above a particular Earth location.

Coarse data obtained from existing mathematical models, such as data pertaining to electromagnetic field strengths between the Van Allen Belts and the Earth, may be stored in database 84. The coarse data may now be refined by combining the detailed real time data stored in database 82 with the mathematical modeled data stored in database 84. Processor 83 may perform the combining of both data from the two databases.

The present invention contemplates providing weather predictions of space to an end user that would be similar to weather predictions available today on the Earth.

Figure 9:
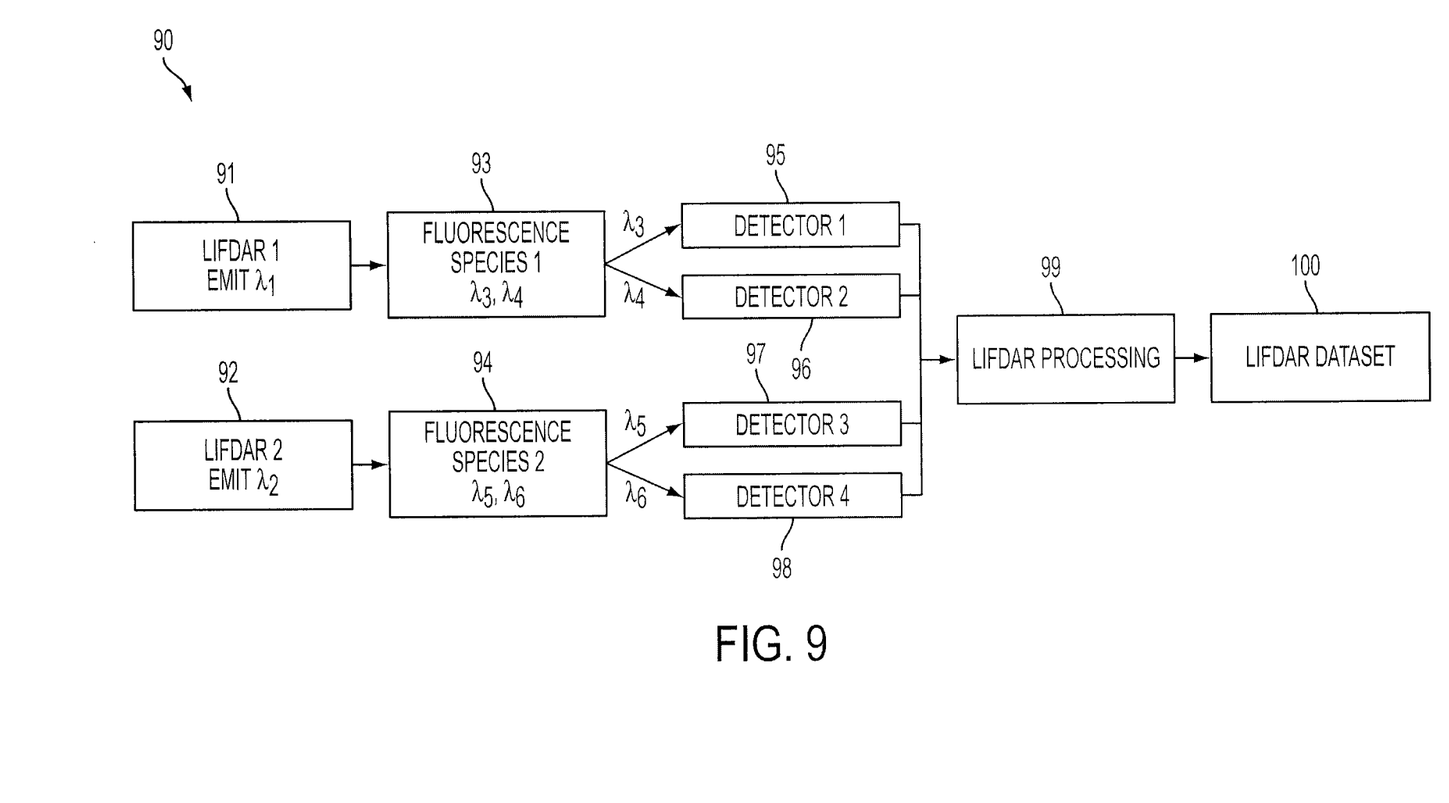
FIG. 9 is a block diagram of two, or more, LIFDAR systems, each used for collecting data of targeted species located in different layers of the magnetosphere, in accordance with an embodiment of the present invention.

Referring next to FIG. 9, there is shown system 90 which includes two LIFDAR systems, 91 and 92. Although only two LIFDAR systems are shown, it will be understood that more than two LIFDAR systems may be used. Furthermore, the LIFDAR systems may be co-located on the Earth or co-located in one satellite in orbit. Alternatively, one system may be located on the Earth and another system may be located in orbit around the Earth. Moreover, each system may include a scanning capability in order to provide azimuth and elevation data for each tuple (x, y, z) captured and stored in dataset memory 100. The scanning capability provides two-dimensional (2D) data with respect to a reference point, while the LIFDAR processor 99 calculates range data to each of the tuples, thereby making three-dimensional data (3D) available for storage. By using a coordinate transformation matrix, referenced to the Earth, processor 99 is able to obtain each tuple of a particular species in an (x, y, z) geo-referenced frame with respect to the Earth.

As shown in FIG. 9, each LIFDAR system transmits a unique wavelength (for example $\lambda_1$ and $\lambda_2$), while simultaneously scanning in azimuth and elevation. Radiation returned from each species fluoresces at a particular wavelength. Using two different wavelengths that are longer than the original transmitted wavelength, the Boltzmann Equation, described earlier, may be solved to obtain the number of atoms or molecules that are singly ionized, thereby leading to density determination of each species as a function of range (see Equation 2).

The radiation returns from respective species, received by corresponding modules 93 and 94, are separately detected by respective detectors 95, 96, 97 and 98, each responsive to a different wavelength. The detected outputs from the multiple detectors are then processed by LIFDAR processor 99 to obtain multiple tuples of (x, y, z) as a function of time (t). Density of each species as a function of range is also computed. Additional data, such as abundance of each species, and demarcation points of each species are also computed. Furthermore, processing the return radiation at different time intervals allows processor 99 to compute temporal variations in each species, including range and velocity vectors for each species, density variations of each species, and abundance variations of each species. The processed data is stored in memory 100, which includes multiple datasets, one dataset for each species.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method for collecting data of species in the magnetosphere comprising the steps of:
   (a) tuning at least one laser to spectral indices of targeted atomic or molecular species located in the magnetosphere;
   (b) measuring fluorescence radiation from each of the targeted species, in response to the tuning step;
   (c) determining range to each of the targeted species; and
   (d) collecting data from the fluorescence radiation for stratifying the targeted species in sequential layers with respect to the Earth.

2. The method of claim 1 wherein
   step (b) includes measuring scattered radiation from each of the targeted species, in response to the tuning step; and
   step (c) includes normalizing the fluorescence radiation based on the scattered radiation; and
   determining the range from the normalized fluorescence radiation to each targeted species.

3. The method of claim 1 wherein
   step (a) includes tuning at least two lasers to multiple wavelengths; and
   step (b) includes determining abundance from the multiple wavelengths returned from the fluorescence radiation of the targeted species.

4. The method of claim 1 including the step of:
   collecting data from the fluorescence radiation for determining temperature of the targeted species.

5. The method of claim 1 including the step of:
   collecting data from the fluorescence radiation for determining drift velocity of the targeted species.

6. The method of claim 1 including the steps of:
   scanning the laser in azimuth and elevation to obtain a 2-dimensional location of the targeted species; and
   obtaining a 3-dimensional location of the targeted species, after determining the range in step (c).

7. The method of claim 1 wherein
   the steps of tuning, measuring and determining of steps (a), (b) and (c), respectively, are performed in a space location, on an Earth location, or in both locations.

8. The method of claim 7 wherein
   at least one laser is located in space and another laser is located on the Earth.

9. A method for obtaining data related to species in the magnetosphere comprising the steps of:
   a) tuning at least one laser to spectral indices of targeted atomic or molecular species located in the magnetosphere;
   b) measuring instantaneous scattering and fluorescence radiation from the targeted species, in response to the tuning step;
   c) determining dynamic range to each of the targeted species producing the scattered radiation;
   d) determining dynamic normalization of the fluorescence radiation from the scattered radiation; and
   e) determining dynamic range based on the normalized fluorescence radiation to each of the targeted species.

10. The method of claim 9 wherein
    the step of tuning the laser includes scanning the laser to different wavelengths based on the targeted species.

11. The method of claim 9 further including one, or more than one, of the following steps:
    identifying the targeted species, based on returned wavelengths of the radiation;
    determining changes in stratification of the targeted species as a function of time;
    determining changes in abundance of the targeted species as a function of time;
    determining changes in temperature of the targeted species as a function of time; and
    determining changes in drift velocity of the targeted species as a function of time.

12. The method of claim 11 including the step of:
    using a mathematical model to determine the changes of the targeted species as a function of time.

13. A method for collecting data of species in the magnetosphere comprising the steps of:
    (a) tuning at least one laser to spectral indices of targeted atomic or molecular species located in the magnetosphere;
    (b) measuring fluorescence radiation from each of the targeted species, in response to the tuning step; and
    (c) determining range to each of the targeted species;
    wherein the steps of tuning, measuring and determining of steps (a), (b) and (c), respectively, are performed in a space location, on an Earth location, or in both locations.

14. The method of claim 13 wherein
    step (b) includes measuring scattered radiation from each of the targeted species, in response to the tuning step; and
    step (c) includes normalizing the fluorescence radiation based on the scattered radiation; and
    determining the range from the normalized fluorescence radiation to each targeted species.

15. The method of claim 13 wherein
    step (a) includes tuning at least two lasers to multiple wavelengths; and
    step (b) includes determining abundance from the multiple wavelengths returned from the fluorescence radiation of the targeted species.

16. The method of claim 13 including the step of:
    collecting data from the fluorescence radiation for stratifying the targeted species in sequential layers with respect to the Earth.

17. The method of claim 13 including the step of:
    collecting data from the fluorescence radiation for determining temperature of the targeted species.

18. The method of claim 13 including the step of:
    collecting data from the fluorescence radiation for determining drift velocity of the targeted species.

19. The method of claim 13 including the steps of:
    scanning the laser in azimuth and elevation to obtain a 2-dimensional location of the targeted species; and
    obtaining a 3-dimensional location of the targeted species, after determining the range in step (c).

20. The method of claim 13 wherein
    at least one laser is located in space and another laser is located on the Earth.

* * * * *